United States Patent
Steele

(12) 
(10) Patent No.: US 6,371,929 B1
(45) Date of Patent: Apr. 16, 2002

(54) METHOD AND APPARATUS FOR PRODUCING STEERABLE COATED GUIDEWIRES AND THE STEERABLE GUIDEWIRES PRODUCED THEREBY

(76) Inventor: Timothy W. Steele, 9 Jay Dr., Rindge, NH (US) 03461

( * ) Notice: Subject to any disclaimer, the term of this patent is extended or adjusted under 35 U.S.C. 154(b) by 0 days.

(21) Appl. No.: 09/818,687

(22) Filed: Apr. 26, 2000

Related U.S. Application Data

(62) Division of application No. 09/082,018, filed on May 20, 1998, now abandoned.

(51) Int. Cl.⁷ .................................................. A61R 5/00
(52) U.S. Cl. ........................................ 600/585; 427/2.3
(58) Field of Search ........................... 600/585; 427/2.3, 427/2.12, 118, 119, 120, 278, 287, 359, 365, 2.28, 160, 277, 203, 205

(56) References Cited

U.S. PATENT DOCUMENTS 4,820,896 A * 4/1989 Weil et al. ...................... 219/83
5,772,609 A * 6/1998 Nguyen et al. ............. 600/585
6,033,720 A * 3/2000 Stolze et al. .................. 427/2.3

* cited by examiner

Primary Examiner—Max Hindenburg
Assistant Examiner—Pamela Wingood
(74) Attorney, Agent, or Firm—George W. Dishong

(57) ABSTRACT

Method and apparatus for producing steerable coated guidewires and the steerable guidewires produced thereby. The steerable coated guidewire has an inner wire member having a constant outer diameter over a major segment thereof and a tapered outer decreasing diameter over a minor segment thereof and a coating adhered to the inner wire member. The coating has a constant outer diameter such that the coated steerable guidewire has a constant outer diameter. The diameter decreases preferably in a linear manner over the length of the minor segment from a maximum diameter $D_{max}$ to a minimum diameter $D_{min}$. The apparatus for producing the guidewires has an extrusion device having an extruder cross-head through which the coated wire advances, preferably a caterpillar haul-off machine for advancing the wire at a haul-off rate controlled by a processor generated control signal, a programmable microprocessor for generating haul-off/take-off control signals, the controlled haul-off rate thereby causing the wire to be coated with variable thickness coating such that the outer diameter of the resulting steerable coated guidewire is substantially constant.

9 Claims, 2 Drawing Sheets

METHOD AND APPARATUS FOR PRODUCING STEERABLE COATED GUIDEWIRES AND THE STEERABLE GUIDEWIRES PRODUCED THEREBY

This application is a division, of application Ser. No. 09/082,018 filed on May 20, 1998 now abandoned.

BACKGROUND

The present invention relates to steerable coated guidewires for introduction into vessels such as blood vessels to aid in placement of devices such as catheters into the vessels. Particularly, the invention relates to a process or method, and apparatus for making coated steerable guidewires having a substantially constant outer diameter and being of contiguous construction from the proximal end to the steerable and flexible distal end. Additionally the invention relates to the steerable coated guidewires produced by the method and apparatus of the invention.

FIELD OF THE INVENTION AND PRIOR ART

Steerable guidewires which are known to the inventor hereof, required either elaborate capping procedures and apparatus for a tapered end of the wire to achieve a very flexible, but constant diameter wire, or they required the use of one or more shape memory alloy wires alone or in combination, annealed to provide steering upon heating of the wires.

An example of a known steerable guide wire for use in medical procedures which requires an elaborate capping procedure comprises a core wire of preferably stainless steel which runs the entire length of the guide wire. The distal end of the core tapers twice to an intermediate and final diameter. The distal tip of the core wire may be flattened to enhance handling and flexibility. A flat wire coil may be in contact with the first taper and is brazed at each end to the core wire. A flexible coil spring is attached to about the most distal 5 cm of the core wire. The spring is tightly wound at its proximal end and more loosely wound at its (and the core wire's) distal end to improve flexibility at the distal tip of the guide wire. At the distal end, the coil spring and the core wire are coextensive and fixedly attached together by a hemispherical weld at the distal tip of the guide wire.

In the manufacture of known steerable guidewires, it has been necessary to manually affix a soft tip on the tapered distal end of the wire. Affixing the tip manually is very labor intensive, very costly and, because the tip is a separate part from the coating on the shaft, a degree of risk exists that the tip could fall off in use, i.e., while inside a vessel of the body.

It would be desirable to have a steerable guidewire the steering or directing of which does not require the use of heat to deform shape memory alloys. It would also be very desirable to have a steerable guide wire which does not require the distal end to be specially designed with springs or other devices and procedures to create a distal end that has a constant diameter but which is very flexible to the extent that it will conform to the direction of the vessel into which it is being inserted.

It would be desirable if a steerable guide wire could be made without excessive processes and procedures involved in the extrusion process of making the constant diameter steerable guidewire thereby potentially improving the constancy of the steerable nature of the guidewire and improving the reliability of the performance of the guidewire.

The following patents show the state of the art in the field of steerable guidewires.

The U.S. Pat. No. 5,211,183 patent to Wilson, (the '183 patent) discloses a steerable memory alloy guide wire for use in positioning medical devices inside the body. The guide wire may be formed of any shape memory alloy or other transitional temperature activated mechanical memory materials. The guide wire is comprised in whole or in part of one or more heat activated memory alloys alone or in combination with one or more non-heat activated materials. The alloy is annealed to particular shapes (for example curves) then cooled and formed into its previously annealed shape. The invention applies the shape memory alloy concept to provide accurate steering capability to guide wires in various forms. Heating of the wire may be by induction, application of RF energy, immersion heating by water, or body temperature. If electrical current is used, the guide wire and any electrical wires may be insulated by a nonconductive sleeve or coating. The shape memory alloy may comprise all or part of a guide wire or multiple wires of memory alloy, annealed to different shapes or curves, may be bound together and used, having been annealed, for example, to work equally in opposite directions, to provide additional steering capability.

The U.S. Pat. No. 5,069,217 patent to Fleischhacker Jr. (the '217 patent) discloses a steerable guide wire for use in medical procedures. The wire is comprised of a core wire of preferably stainless steel which runs the entire length of the guide wire. The distal end of the core tapers twice to an intermediate and final diameter. The distal tip of the core wire may be flattened to enhance handling and flexibility. A flat wire coil may be in contact with the first taper and is brazed at each end to the core wire. A flexible coil spring attached to about the most distal 5 cm of the core wire. The spring is tightly wound at its proximal end and more loosely wound at its (and the core wire's) distal end to improve flexibility at the distal tip of the guide wire. At the distal end, the coil spring and the core wire are coextensive and fixedly attached together by a hemispherical weld at the distal tip of the guide wire. The hemispherical tip provides for smooth insertion and maneuvering of the wire. The main body of the core wire, proximal to the first taper may be coated with a polymer to improve handling characteristics. However, the most proximal end of the guide wire and the distal end with the coiled spring may be left uncoated—there then results in some small net taper of the outer diameter of the guide wire as a whole from the coated portion to the uncoated tip.

The U.S. Pat. No. 5,025,799 patent to Wilson (the '799 patent), a division of the above-mentioned Wilson U.S. Pat. No. 5,211,183 patent, the difference being the claims. The claims of this patent are directed to the guide wire being comprised of at least one solid elongated strand constructed of shape memory alloy material wherein at least one portion along the length of the strand is annealed to affect a shape change upon application of heat. The claims of the above '183 patent are directed to a guide wire comprising at least a pair of solid elongated shape memory wire members held in substantial coaxial engagement with each other but so as to allow relative sliding movement between the two, wherein one of the wire members is annealed to under go a shape change in one direction and another is annealed to undergo a shape change in another direction, the guidewire as a whole being rotatable to enable omnidirectional steering of the guide wire.

The U.S. Pat. No. 5,800,890 patent to Cramer (the '890 patent) discloses a steerable guide wire for catheters, which may be a combination catheter and guide wire. The guide wire is composed of a hollow metal guide tube through which liquid may flow. The guide tube is made of a plurality of tapering metal tube sections, each section tapering from proximal to distal end and each succeeding proximal end insertable into the preceding distal end and soldered together to form one tapering guide tube. Attached to the distal end of the tube is a helically wound spring, overlapping (for stability) a substantial part of the distal end of the guide tube but extending beyond the distal end of the guide tube. The distal end of the spring has a rounded cap. There is also a fine wire attached at the cap end of the spring and running to the proximal end of the spring where it is also attached to the spring. The wire provides stability and prevents the spring form being over-extended and causing damage to the vessel into which it is inserted. There may also be included a turning handle at the proximal end of the guide tube for steering and placement of the tube. There are then disclosed several applications of use of the steerable guide wire/guide tube including applications in which there is a connector, at the proximal end of the guide tube, for an injection adapter so that fluid may be injected through the guide wire/guide tube.

The U.S. Pat. No. 4,719,924 patent to Crittendon et al. (the '924 patent) discloses a small diameter steerable guide wire with an adjustable tip. The guide wire is comprised of a tubular main wire tapering to its distal end, an outer helical outer spring attached at and extending beyond the distal end of the main wire, a distal core wire attached to the distal end of the main wire and tapering to its own distal end. The outer spring also extends beyond the distal end of the distal core wire. The outer diameter of the outer spring is approximately that of the main wire before the main wire tapers. There is a rounded cap at the end of the outer spring. There is also an inner, safety, spring extending from the distal portion of the distal core wire to the distal end of the outer spring—where there is no wire inside the outer spring. There is a pull wire attached to the cap at the distal end of the guide wire, the pull wire extending through the lumen of the helical outer spring, and between the outer spring and the distal core wire until it reaches the joint between the main wire and the distal core wire. There is an opening in the tubular main wire through which the pull wire passes into the lumen of the main wire and out the proximal end where there is a means for retaining the pull wire in position, and for rotationally and bendably adjusting the distal tip shape and from by use of the pull wire. The wires and springs may be made of stainless steel.

The U.S. Pat. No. 4,676,249 patent to Arenal et al. (the '249 patent) discloses an optionally bendable and flexible guide wire. The guide wire is comprised of three main components; an elongate coiled wire body having a lumen and capable of forming an arctuate shape at its distal end, a tapered curve control wire disposed inside the lumen of the coiled wire body and a stiffening member disposed inside the lumen of the coiled wire body but outside the curved control wire. The coiled wire body is composed of helically wound coils and has a curved cap on its distal end. The curved control core wire tapers towards its distal end and has a hemispherical end. The distal end of the curved control core wire is sufficiently stiff to lend rigidity to the coiled wire body. The curve control core wire is preferably made of stainless steel. The curve control wire and the stiffening member are slidable with respect to each other and with respect to the coiled wire body. The coiled wire body is preferably plastic-coated stainless steel.

The U.S. Pat. No. 4,068,615 patent to LeNir (the '615 patent) discloses a digital computer control for a wire coating line primarily directed at insulated electrical wires. The speed of the wire passing through a conventional extruder is controllable, the rate and temperature of the extruded plastic coating are controlled, and the distance of the cooling means from the coating means is controllable. These controllable factors affect both the capacitance and diameter of the coated wire produced. The capacitance or diameter of the coated wire is measured, provided as a digital value to a control computer which compares the received value to a control valve and then the operating characteristics of the line are altered to provide wire of the desired capacitance or diameter. There is an extruder screw, the RPM of which may be controlled in response to either measured versus control capacitance or diameter of the extruded wire. The application of the control system is mainly to plastic coated insulated electrical wires. The control process seems to be able to vary the thickness of the plastic coating slightly to achieve a uniform outer diameter on an essentially uniform diameter inner wire.

The U.S. Pat. No. 3,893,642 patent to Van Vlaenderen (the '642 patent) is a Continuation-in-Part of an abandoned application and discloses polyethylene terephthalate plastic coated wire for use primarily in the manufacture of barbed wire, wire mesh, wire netting, wire fences and the like. The disclosure of the process of making the wire is essentially the same as the related '545 patent discussed below. The process produces wire with polyethylene terephthalate plastic coating which is at least 95% up to 98% amorphous. The process produces a rather large diameter wire which is not used in delicate medical applications. The U.S. Pat. No. 3,829,545 patent to Van Vlaenderen (the '545 patent) discloses essentially the same process and produces essentially the same products as the above '642 patent. In a preferred embodiment of this invention, a heated wire is passed through an extrusion head in which molten plastic is extruded under pressure to form a coating on the wire to produce coated wire. The wire is preheated by any conventional technique, for example electrical heating. The wire is continuously passed from a storage spool to a heater and then to the extrusion head of the extrusion machine. The operation is continuous, and the preheating of the wire is on a continuous basis. There is an Archimedes screw in a heated cylinder in the extrusion machine through which plastic grains pass and become more and more plastically deformable. The heated plastic is pushed forward while being increasingly compressed. The thickness of the plastic coatings on the wire may be regulated by using differently sized extrusion heads as well as controlling the pressure produced by the Archimedes screw. Immediately after extrusion, the plastic coated wire is chilled, preferably by cold water to maintain a plastic coated steel wire of which the coating is preferably at least 80% amorphous. The coating has a thickness of about 0.1 to 0.3 mm, and the invention is particularly applicable to metal wires having a diameter greater than 1.0 mm. The claims are directed to an improved process for manufacturing the wire.

SUMMARY OF THE INVENTION

The most basic embodiment of the present invention discloses a constant diameter coated steerable guidewire and a method and apparatus to produce the steerable guidewire. The invention provides an inner wire member which tapers—preferably linearly—over a minor segment or portion of the inner wire member where the linearly tapered minor segment is located at least one end of the inner wire member. A coating is applied to the wire wherein the outer diameter of the coated wire remains constant despite the taper of the inner wire member. The amount of coating is increased proportionately as the diameter of the inner wire member decreases so that the resulting steerable guidewire has a constant outer diameter. Thus the flexibility and steerability of the resulting steerable guidewire is increased by tapering the inner wire member, but the finished coated wire maintains a constant outer diameter.

One embodiment of the present invention provides a coated steerable guidewire comprising an inner wire member having a constant outer diameter over a major segment of the inner wire member and a tapered (preferably linearly tapered) outer diameter over a minor segment of the wire member, the minor segment located at one end of the inner wire member; and a coating adhered to the inner wire member, the coating having a constant outer diameter such that the resulting coated steerable guidewire has a constant outer diameter.

There is also provided a method for producing a constant outer diameter coated steerable guidewire comprising the steps of advancing wire having at least one end with a linearly tapering outer diameter, through an extrusion device having a cross head/extrusion head; detecting an outer diameter of the wire as it passes into the cross head; depositing molten coating material on the wire as the wire passes through the cross head thereby producing a coated wire; cooling the coated wire; hauling off the coated wire; and controlling the advancing and depositing with a programmable microprocessor such that the constant outer diameter coated steerable guidewire is produced. The programmable microprocessor is controlled by software code which causes the microprocessor to slow the rate of feed and haul-off of the wire through the cross head when a decrease in outer diameter of the wire is detected, such that more coating is deposited as the outer diameter of the wire decreases so that the resulting coated wire has a constant outer diameter.

Another embodiment of the present invention is an apparatus for producing coated steerable guidewire of constant outer diameter comprising a programmable microprocessor which provides control signals to an extrusion apparatus having a controllable means for advancing wire through the extrusion apparatus, the extrusion apparatus comprising; a cross head/extrusion head through which the wire passes; a detecting device for detecting outer diameter of the wire as the wire passes into the cross head and for providing signals to the programmable microprocessor; at least one coating apparatus which provides molten coating material into the cross head to coat the wire as the wire passes through the cross head; a cooling means which cools the wire coated with the coating material after the wire passes out of the cross head; and a haul-off device for removing the wire from the cooling means, thereby producing the coated flexible guidewire. The wire has at least one end thereof having a linearly decreasing outer diameter decreasing from $D_{max}$ to $D_{min}$ over a linearly tapering portion of length $L_t$ of the wire. The detecting device detects the linearly decreasing outer diameter of the wire, and the detecting device is preferably a laser monitor. The microprocessor controls a rate at which the extrusion apparatus advances the wire in response to the signals provided by the detection device wherein the rate is decreased by the microprocessor as the outer diameter of the wire decreases, and a thickness of the coating material is thereby increased such that the coated steerable guidewire has a constant outer diameter.

In yet another embodiment, there is provided a constant outer diameter coated steerable guidewire produced by a process comprising the steps of advancing wire having at least one end with a linearly tapering outer diameter, through an extrusion device having a cross head/extrusion head; detecting an outer diameter of the wire as it passes into the cross head; depositing molten coating material on the wire as the wire passes through the cross head thereby producing a coated wire; cooling the coated wire; hauling off the coated wire; and controlling the advancing and depositing with a programmable microprocessor thereby producing the constant outer diameter coated steerable guidewire.

An aspect of the present invention is to provide a coated steerable guidewire which has a tapered inner wire member and a constant outer diameter.

Another aspect of the invention is to provide a method for producing a constant outer diameter coated steerable guidewire which has a tapered inner wire member.

Yet another aspect of the invention is to provide a steerable guidewire which does not require elaborate capping or tipping to achieve flexibility and steerability while maintaining a constant outer diameter of the guidewire.

Still another aspect of the invention is to provide a steerable guidewire made from "simple" starting materials which do not require special annealing procedures to produce steering capability and which do not require heating of the wire during insertion into body vessels such as blood vessels to achieve steerability.

These and further objects of the present invention will become apparent to those skilled in the art after a study of the present disclosure of the invention and with reference to the accompanying drawings which are a part hereof, wherein like numerals refer to like parts throughout, and in which:

DETAILED DESCRIPTION OF THE PREFERRED EMBODIMENT

Clearly, it is obvious that many wire diameters, taper profiles, wire lengths and constant outside diameters of the coated guidewire 10 are possible. All of the aforementioned variables are a function of particular applications such as the size of the vessel into which the guidewire is to be placed, the amount and the type of deflections that are required in order for the guidewire to safely enter the vessels, and the like. However, the basic structure of guidewire 10 is the same—a wire member having one end with a varying diameter over a minor portion thereof and wire member 16 having a coating 17 thereon resulting in guidewire 10 having a substantially constant outside diameter over the entire length of guidewire 10.

The apparatus 20 may have variations with regard to particular hardware and software devices. Clearly, however, there is provided a speed controllable means for pulling the wire, a means for sensing wire member diameters, means for comparing the wire member diameter to a program which defines haul-off speed as a function of wire member diameter and a means for processing the signals generated which signals are indicative of wire member diameter to create a constant diameter coated steerable guidewire which coating is put onto wire member 16 by an extrusion device known to those skilled in the field of wire coating.

The construction and the design of substantially constant diameter coated steerable guidewire 10, and variations thereof, will be described with reference to FIGS. 1 and 2 collectively. The coated steerable guidewire may vary in length from about 6 inches to any length that is needed to provide for the function of the guidewire within the body. While there may be a minimum useful length for guidewires, the minimum length is dictated only by the apparatus which is used to coat the wire. The inner wire member is preferably formed from stainless steel, but may be made of any suitable alloy or material providing the needed flexibility and surface characteristics which will permit coating of the wire. The coating is preferably a thermoplastic having the necessary characteristics which permit use within a vessel within the body and which is attachable to the outer surface of the wire which is to be coated with the coating material.

Figure 2:
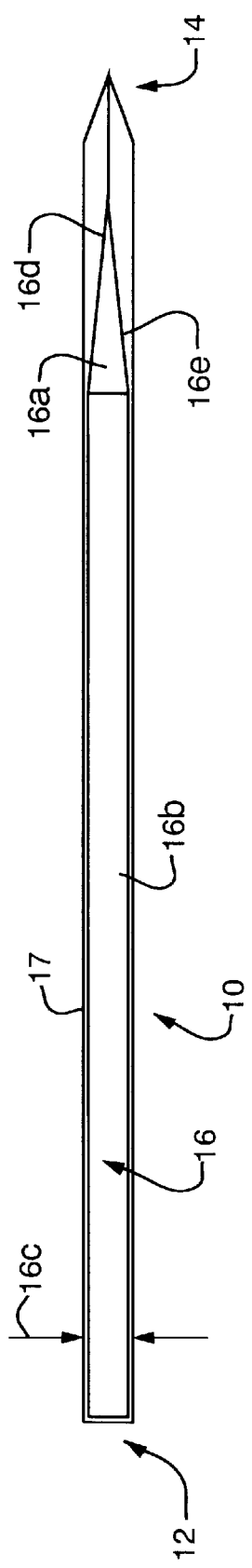
FIG. 2 is a sketch of the coated steerable guidewire produced by the method and the apparatus of the present invention.

Constant diameter coated steerable guidewire 10 is shown in FIG. 2 having a predeterminable length and diameter. Guidewire 10 has a guidewire proximal end 12 and a guidewire distal end 14. There are basically three fundamental components to guidewire 10, wire member 16 having a tapering segment or tapering portion 16A with a minimum diameter 16D, constant diameter segment or major portion 16B with a maximum diameter 16C and a coating 17 extruded or otherwise placed onto wire 16 in a manner so as to result in guidewire 10 having the constant diameter feature. Clearly, in the most general sense, wire member 16 need not have tapering portion 16A be located at one end such as distal end 14—it could be located anywhere along the length of wire 16. Tapered portion 16A is illustrated as having a linear profile but the taper profile 16E could be non-linear such as for example exponential or logarithmic depending on the flexing characteristics which may be desired in guidewire 10.

Figure 1:
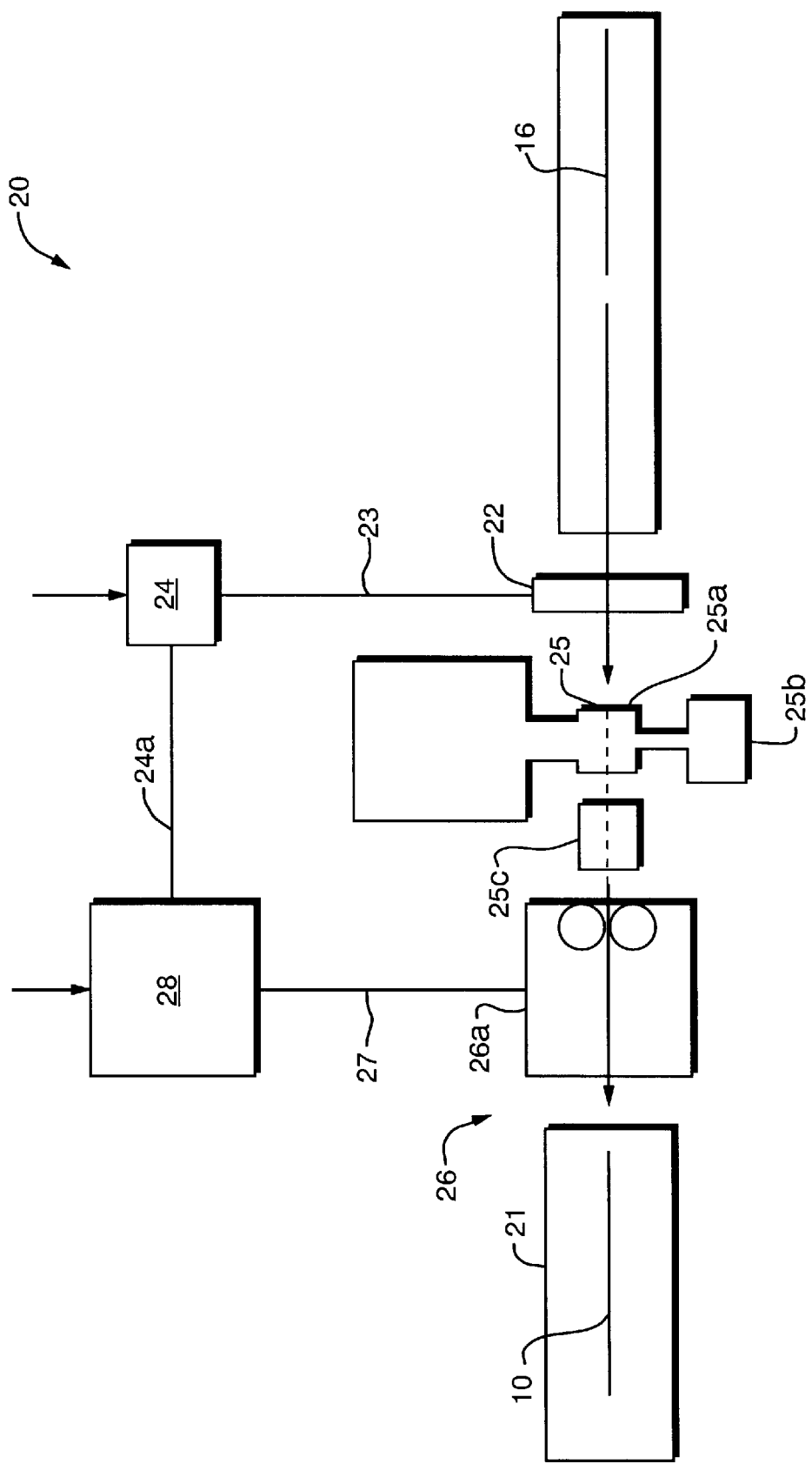
FIG. 1 is a schematic representation of the apparatus used to produce the guidewire.

FIG. 1 is a schematic representation of apparatus 20 which may be used to make guidewires 10. What is illustrated is a storage device 21 for storing wire members 16. When a wire member 16 is to be coated in such a manner as to result in guidewire 10, a wire member is place in such a manner as to have the diameter of the wire measured by diameter gauge 22 which, through diameter gauge-diameter gauge microprocessor interface 23 is in data flow communication with diameter gauge microprocessor 24 for energizing diameter gauge 22 and sensing signals representing the diameter of the portion of wire member 16 passing within diameter gauge 22. Wire member 16 is caused to pass from diameter gauge 22 into extruder 25 and particularly into coating head or cross head 25A. In order to improve coating consistency a vacuum system 25B may be incorporated as a part of extruder 25. Cooling device 25C, such as a water trough, may be used to control the cooling of coating 17 which coating 17 is on the coated wire member 16.

To cause wire 16 to be advanced through gauge 22 and extruder 25, a haul-off 26 having microprocessor controllable haul-off speed may be used. There is a haul-off speed microprocessor 26A which controls the haul-off speed, that is, the speed in feet-per-minute (FPM) at which wire 16 advances through apparatus 20. Haul-off speed microprocessor 26A is in data-flow communication with control computer 28 through haul-off microprocessor-control computer interface 27. Control computer 28 stores a prepared speed interruption program loop and processes signals from diameter gauge microprocessor 24 via diameter gauge-control computer interface 24A and from haul-off speed microprocessor 26A via haul-off microprocessor-control computer interface 27 and controls the haul-off speed as a function of the stored program loop and the microprocessor signals to create constant diameter coated steerable guidewire 10.

How the Process Works

The thermoplastic coating 17 on guidewire 10 is extruded or coextruded on the surface of wire 16. To maintain a uniform outside diameter of plastic coating on wire 16 the linear (travel) speed "X" of the wire passing through crosshead 25A must remain constant along constant diameter portion 16B of the wire and then slow down as the tapered distal end 16A of wire 16 enters the thermoplastic extrudate in coating head 25A of extruder 25. As the linear speed of the wire slows a thicker and thicker coating of plastic is extruded on the tapered wire diameter and in this way the overall diameter of the coated wire is held constant.

As depicted in the schematic of the extrusion line ie., apparatus 20, haul-off 26, diameter gauge 24, and control computer 28 are electronically interfaced. I.e., diameter gauge-diameter gauge microprocessor interface 23, diameter gauge-control computer interface 24A and haul-off microprocessor-control computer interface 27 are all designed to provide the required input and output signals needed by apparatus 20. By using a computer program uniquely modified for this application the linear speed of the wire can be controlled. The program is designed to run intermittently on command/signal from the diameter gauge microprocessor which permits the processing of separate/individual pieces/lengths of wire one at a time. The signal used is the alarm signal that is generated when the diameter gauge senses that the diameter of the wire has changed (The tapered diameter has fallen below a programmed value). When this signal is sent to the haul-off microprocessor the constant line speed is interrupted to run the programmed speed changes to maintain the coating diameter as specified. When the programmed loop finishes the haul-off is returned to the original line speed for coating the wire shaft and the haul-off microprocessor waits for the next signal to run the programmed speed interruption. A vacuum is usually utilized inside the crosshead wire channel to insure that the thermoplastic has good adhesion to the wire.

An example of a speed interruption program loop may be as follows. Note that displacement=X (measured linearly in inches), haul-off speed=S (Feet per minute, FPM)

| | |
|---|---|
| Line 1 X = 0.00" | S = 35.00 FPM |
| Line 2 X = 12.00" | S = 35.00 FPM |
| Line 3 X = 16.00" | S = 15.00 FPM |
| Line 4 X = 20.00" | S = 10.00 FPM |
| Line 5 X = 26.00" | S = 35.00 FPM |
| Line 6 X = −1.00" | |

Explanation of the program loop is as follows.

All machines are running with wires to be coated. The haul-off is running at 35.00 FPM as indicated in program lines #1 and #5. A wire is fed through the diameter gauge and into the extrusion crosshead and thermoplastic extrudate being emitted from the end of the extrusion die. The diameter gauge continually scans and monitors the diameter of the wire. The diameter gauge microprocessor has been programmed to signal an alarm if the diameter of the wire varies more than a specified amount. When the tapered (or stepped) end of the wire enters the scan of the diameter gauge the smaller diameter of the wire is sensed and the diameter gauge microprocessor signals the haul-off and the programmed loop starts running starting with line #1.

Line #1: The tapered end has entered the diameter gauge scan but the beginning of the taper is still 12.00 inches upstream from the point at which plastic is placed on the wire. The haul-off is to start running the programmed speed interruption loop. Displacement is 0.00 inches and the linear speed of the haul-off continues at 35.00 FPM until the next programmed displacement and speed change specified in Line #2 of the program, which is the point at which the wire diameter taper begins and additional plastic must be placed on the wire to maintain a constant outside diameter—OD.

Line #2: The haul-off has moved the wire 12.00 inches @ 35.00 FPM and the taper is now in the extrudate. Line #2 directs the haul-off to ramp (slow) down to the speed and displacement programmed in Line #3 of the loop.

Line #3: The haul-off has moved the wire 4.00 inches and slowed to a rate of 15.00 FPM, thus beginning to extrude a thicker coating of plastic on the taper of the wire. Having reached 16.00 inches displacement haul-off looks to Line #4 for a new speed and displacement.

Line #4: Between 16.00 inches and 20.00 inches the haul-off ramps down more to a linear speed of 10.00 FPM which increases the thickness of the plastic coating on the tapering portion of the wire. At 20.00 inches the haul-off looks to line #5 for a new displacement and speed. At this point the smallest end of the wire has exited the extrusion crosshead and the programmed loop must be closed in preparation for the next wire.

Line #5: Between 20.00 inches and 26.00 inches displacement the haul-off ramps up to the original speed of 35.00 FPM and waits for the next signal to run the speed interruption loop.

Clearly, the program loop discussed above is only representative of programmed speed interruption loops which may be used. The number of Lines, the displacement length where change in speed is to take place (X) and the haul-off speed (S) are all a function of: a) the length of the wire; b) the length of the tapered portion (and the rate of change in diameter of the tapered portion of the wire); c) the diameter of the wire; and d) the final OD desired for the coated guidewire produced.

It is also thought that guidewire 10, apparatus 20, the products produced by apparatus 20 and the use, and manner of use and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

What is claimed is:

1. An apparatus for producing coated steerable guidewire of constant outer diameter comprising:
    a programmable microprocessor which receives data from and provides control signals to an extrusion apparatus having a controllable means for advancing a wire through said extrusion apparatus, said extrusion apparatus comprising;
    an extrusion head through which said wire passes;
    a detecting device for detecting an outer diameter of said wire as said wire passes into said extrusion head and for providing signals to said programmable microprocessor;
    at least one coating apparatus which provides molten coating material into said extrusion head to coat said wire as said wire passes through said extrusion head; and
    a cooling means which cools said wire coated with said coating material after said wire passes out of said extrusion head, thereby producing said coated flexible guidewire.

2. The apparatus according to claim 1 wherein said controllable means for advancing a wire through said extrusion apparatus comprises a haul-off device.

3. The apparatus according to claim 2 wherein said wire has at least one end thereof having a decreasing outer diameter decreasing from $D_{max}$ to $D_{min}$ over a tapering portion of length $L_t$ of said wire.

4. The apparatus according to claim 3 wherein said detecting device detects said decreasing outer diameter of said wire.

5. The apparatus according to claim 3 wherein said detecting device is a laser monitor.

6. The apparatus according to claim 4 wherein said microprocessor controls a rate at which said extrusion apparatus advances said wire in response to said signals provided by said detection device wherein said rate is caused, by said microprocessor, to decrease as said outer diameter of said wire decreases, and a thickness of said coating material is thereby increased such that said coated steerable guidewire has a constant outer diameter.

7. A method for producing a constant outer diameter coated steerable guidewire comprising the steps of:
    advancing a wire having at least one end with a tapering outer diameter, through an extrusion device wherein the rate of advance is controlled as a function of an outer diameter of said wire;
    detecting said outer diameter of said wire as it advances into said extrusion device;
    depositing molten coating material on said wire as said wire passes through said extrusion device thereby producing a coated wire;
    cooling said coated wire; and
    controlling said advancing and said depositing such that said constant outer diameter coated steerable guidewire is produced.

8. The method for producing a constant outer diameter coated steerable guidewire according to claim 7 wherein said step of controlling is done with a programmable microprocessor.

9. A constant outer diameter coated steerable guidewire produced by a process comprising the steps of:
    advancing a wire having at least one end with a tapering outer diameter, through an extrusion device wherein the rate of advance is controlled as a function of an outer diameter of said wire;
    detecting said outer diameter of said wire as it advances into said extrusion device;
    depositing molten coating material on said wire as said wire passes through said extrusion device thereby producing a coated wire;
    cooling said coated wire; and
    controlling said advancing and said depositing such that said constant outer diameter coated steerable guidewire is produced.

* * * * *